United States Patent
Baltas et al.

(10) Patent No.: US 7,517,869 B2
(45) Date of Patent: Apr. 14, 2009

(54) FLUOROPHOSPHONOCINNAMIC COMPOUNDS, SYNTHESIS AND USES FOR TREATING DISORDERS CAUSED BY OXIDATIVE STRESS

(75) Inventors: Michel Baltas, Castanet Tolosan (FR); Florence Bedos-Belval, Donneville (FR); Hubert Duran, Toulouse (FR); Caroline Lapeyre, Tarbes (FR); Anne-Elisabeth Negre-Salvayre, Ramonville (FR)

(73) Assignee: Centre National de la Recherche Scientifique (C.N.R.S.), Paris (FR)

( * ) Notice: Subject to any disclaimer, the term of this patent is extended or adjusted under 35 U.S.C. 154(b) by 15 days.

(21) Appl. No.: 11/664,522

(22) PCT Filed: Sep. 26, 2005

(86) PCT No.: PCT/FR2005/002376

§ 371 (c)(1),
(2), (4) Date: Apr. 3, 2007

(87) PCT Pub. No.: WO2006/037869

PCT Pub. Date: Apr. 13, 2006

(65) Prior Publication Data

US 2008/0090786 A1 Apr. 17, 2008

(30) Foreign Application Priority Data

Oct. 4, 2004 (FR) .................................. 04 10448

(51) Int. Cl.
*A01N 66/00* (2006.01)
*A61K 31/66* (2006.01)
(52) U.S. Cl. ...................... 514/134; 530/359; 558/207
(58) Field of Classification Search ................ 514/134; 530/359; 558/207
See application file for complete search history.

(56) References Cited

U.S. PATENT DOCUMENTS 2,962,517 A 11/1960 Tuppack et al.

FOREIGN PATENT DOCUMENTS

| DE | 301662 | 5/1993 |
|---|---|---|
| SU | 873120 | 10/1981 |
| WO | 94/19358 | 9/1994 |

OTHER PUBLICATIONS

Lapeyre et al., Synthesis of phosphonocinnamic thioesters, substrate analogues of cinnamoyl-CoA reductase, a key enzyme in the lignification process, Tetrahedron Letters (2003), 44(12), 2445-2447.*

"A Facile Conversion of Thio- and Selenophosphoric Acids and their Derivatives into Fluoridates by Means of Reaction with Silver Fluoride", Chroworos et al., Tetrahedron Letters 40 (1999) 9337-9340.

"Rational Inhibitor Design, Synthesis and NMR Spectroscopic Study by Transferred Nuclear Overhauser Spectroscopy of Novel Inhibitors of Cinnamyl Alcohol Dehydrogenase, A Critical Enzyme in Lignification", Kennedy et al., (1999) J. Enzyme Inhibition, 14:217-237.

"Synthesis of Phosphonocinnamic Thioesters, Substrate Analogues of Cinnamoyl-CoA Reductase, a Key Enzyme in the Lignification Process", Lapeyre et al., 2003, Tetrahedron Letters, 44:2445-2447.

Triethylamine Tris(Hydrogen fluoride): Applications in Synthesis, McClinton, 1995, Aldrichimica Acta, 28(2):31-35.

"Cyclohexyl Alkylphosphonofluoridates," Hafner et al., Journal of Medicinal Chemistry, vol. 13, No. 5, 1970 p. 1025, XP002374501.

* cited by examiner

*Primary Examiner*—Daniel M Sullivan
*Assistant Examiner*—Chukwuma O Nwaonicha
(74) *Attorney, Agent, or Firm*—Young & Thompson

(57) ABSTRACT

Process for the specific fluorination of the phosphorus atom of a phosphonocinnamic compound of the general formula (II) or (II'):

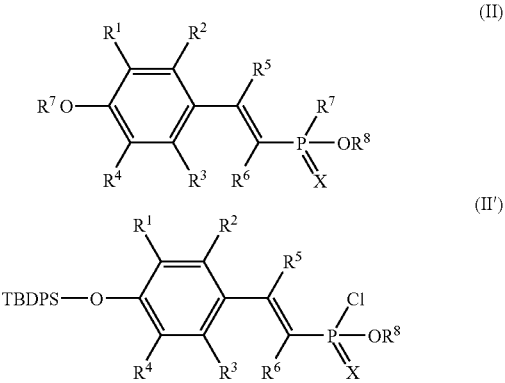

Figure 3:
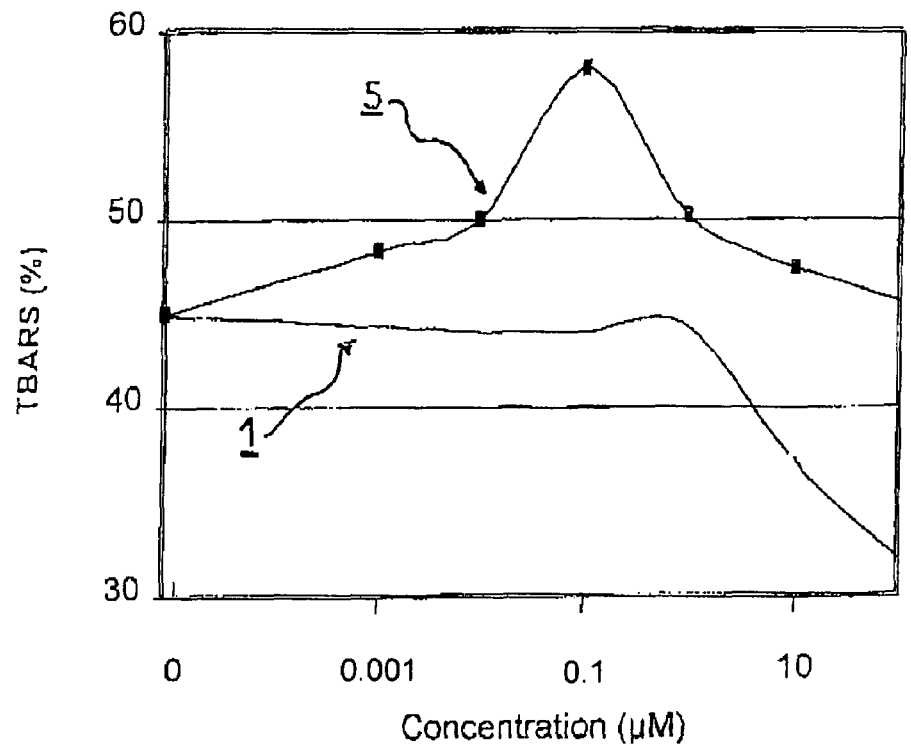

X being selected from: an oxygen atom, a sulfur atom,
$R^1$, $R^2$, $R^3$, $R^4$, $R^5$ and $R^6$ being selected from: H, an alkyl group, an aryl group, OH, O-alkyl, S-alkyl, $NH_2$, NH-alkyl, N-(alkyl)$_2$;
$R^7$ being selected from: H, an alkyl group, an aryl group, a silyl group;
$R^8$ being selected from: H, an alkyl group, an aryl group,
TBDPS representing a tert-butyldiphenylsilyl group; in the process the compound is reacted with a fluorinating agent comprising a complex formed between a tertiary amine and hydrogen fluoride.

14 Claims, 2 Drawing Sheets

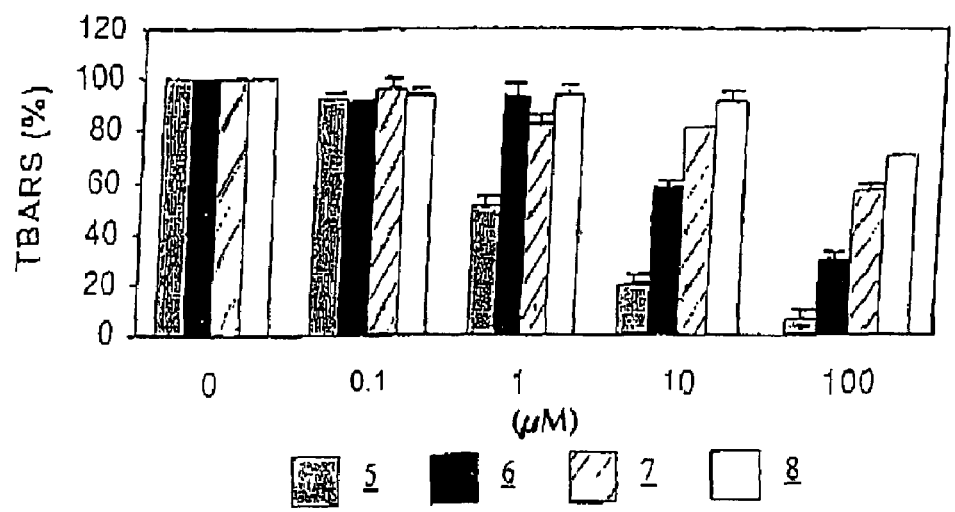
Figure 1A
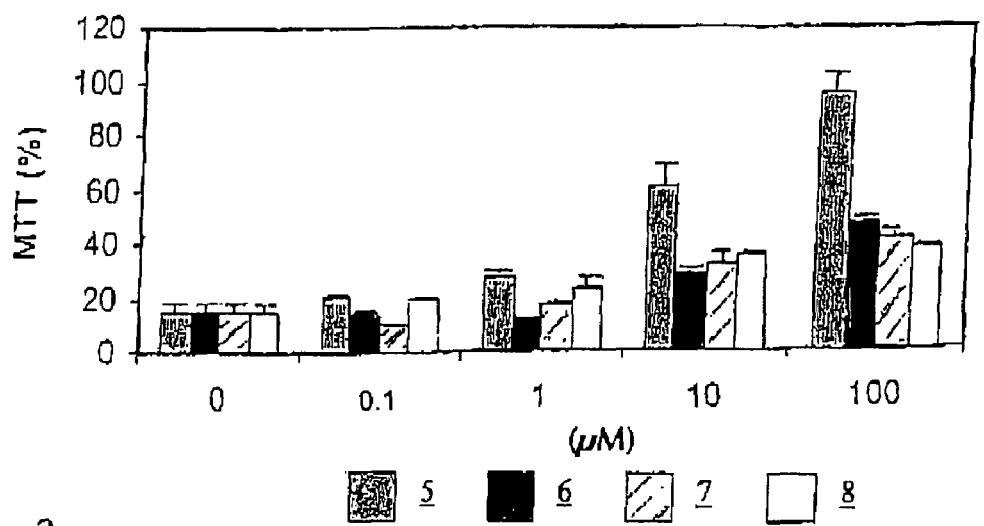
Figure 1B
Figure 2
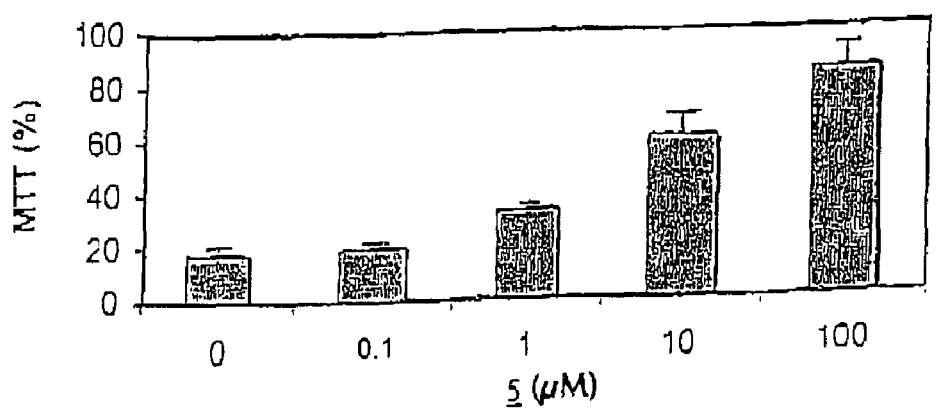

FLUOROPHOSPHONOCINNAMIC COMPOUNDS, SYNTHESIS AND USES FOR TREATING DISORDERS CAUSED BY OXIDATIVE STRESS

The invention relates to a process for the preparation of organofluorophosphorus compounds. It relates more precisely to a novel method for fluorinating organophosphorus compounds and to the synthesis of fluorophosphonocinnamic compounds. These fluorophosphonocinnamic compounds, which are themselves novel, especially owing to their antioxidant activity, have very particular commercial importance, especially in the medical and/or cosmetic fields.

At present, numerous organofluoro(thio)phosphorus esters are known, which can be represented generally by the following formula:

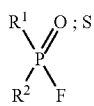

in which $R^1$ and $R^2$ may denote very varied radicals: alkyl, aryl, alkoyl, amide, anilide, etc.

These esters are generally described as enzymatic acylation reaction inhibitors, which are particularly effective on acetylcholinesterases. In addition, owing to their bactericidal and fungicidal power, they are conventionally used in the development of insecticidal and/or disinfectant compositions.

Chworos et al., 1999 (Tetrahedron Letters, 40:9337-9340) describe the preparation of particular organofluorophosphorus esters in which $R^1$ and $R^2$ denote radicals of the phenyl, methoxy, ethoxy and/or tert-butylmethoxy type.

The preparation of these compounds comprises a reaction between compounds of the type phosphino(thio)selenoate, phosphino(thio)chloridate, or their phosphono- or phosphoro-analogs, and silver fluoride (AgF). The reaction is carried out in solution (preferably in trichloromethane or methylnitrile) and can be conducted at ambient temperature. The product of interest is obtained in the form of an insoluble precipitate of dark gray color. It is recovered after dilution of the mixture in dichloromethane, followed by washing with brine and drying over magnesium sulfate.

Although the fluorination method described by Chworos et al., 1999, is simple and rapid to carry out, it nevertheless has two major disadvantages. The first disadvantage is associated with the reagent used, silver fluoride, which is a particularly expensive reagent. Another disadvantage is that it is not possible by this method to obtain compounds of the fluorothiophosphorus type, only compounds of the fluorophosphorus type. Even starting from a compound of the thiophosphonate type, fluorination by means of silver fluoride is also accompanied by conversion of the thiophosphonate function into a phosphonate function and ultimately results in the formation of a fluorophosphorus compound.

U.S. Pat. No. 2,962,517 describes another method for preparing organofluorophosphorus esters and organofluorothiophosphorus esters, in particular compounds corresponding to the following general formula:

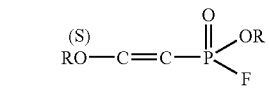

R denoting radicals of the alkyl type.

To this end, a reaction is carried out between a β-alkoxy- or β-alkoyl-mercaptovinyl-phosphonic acid dichloride and alkaline fluorides in the presence of an anhydrous alcohol and of a solvent of the benzene, toluene or chlorobenzene type. The alkaline fluorides (especially sodium fluoride) must preferably be anhydrous and in the finely divided state. The reaction temperature is of the order of from 60 to 90° C.

Not only does the process in question require the handling of benzene, toluene or chlorobenzene, that is to say of solvents that are particularly volatile, inflammable, carcinogenic and noxious, especially by inhalation and by cutaneous contact, but, in addition, it is necessary to heat the reaction medium and therefore to heat those substances whose dangerousness is expressly indicated even at ambient temperature.

Within this context, the object of the invention is to propose a process for the fluorination of organophosphorus compounds, including organothiophosphorus compounds, to form corresponding fluoro(thio)phosphorus compounds, the implementation of which process does not require the use of any substance that poses a serious risk to health or any danger when handled under the normal implementation conditions of said process.

In particular, the invention aims to permit the fluorination, by a process that is simple and rapid to carry out, of particular organo(thio)phosphorus compounds, in the present case of (thio)phosphonocinnamic compounds, for which attempts at fluorination have hitherto been envisaged only rarely, if at all.

Another object of the invention is to be able to propose novel chemical compounds so synthesized that have a commercial application of very particular importance and a potential that is substantially improved as compared with corresponding or analogous non-fluorinated compounds.

In the following text, and according to the context, the terms "phosphorus", "phosphoric", "phosphonic", etc. will be used either specifically to denote phosphorus groups in which the phosphorus atom is bonded by a double bond to an oxygen atom, or more generally to include also the possibility that said phosphorus atom may also be bonded, by a double bond, not to an oxygen atom but to a sulfur atom (in other words, "phosphorus", "phosphoric", "phosphonic", etc. may likewise and optionally be understood as meaning, respectively, "thiophosphorus", "thiophosphoric", "thiophosphonic", etc.).

The invention relates to fluorophosphonocinnamic compounds of the general formula:

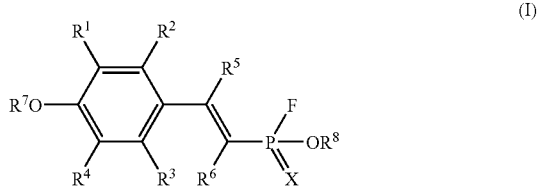

in which:

X is selected from:
   an oxygen atom and a sulfur atom, $R^1$, $R^2$, $R^3$, $R^4$, $R^5$ and $R^6$ are selected from:
   H, an alkyl group, an aryl group, OH, O-alkyl, S-alkyl, $NH_2$, NH-alkyl, N-(alkyl)$_2$, $R^7$ is selected from:
   H, an alkyl group, an aryl group, a silyl group, $R^8$ is selected from:
   H, an alkyl group, an aryl group, and in which said alkyl and aryl groups contain of the order of from 1 to 6 linearly bonded carbon atoms.

According to the invention, these fluorophosphonocinnamic compounds of the general formula (I) can be obtained by fluorination of phosphonocinnamic compounds of the general formula:

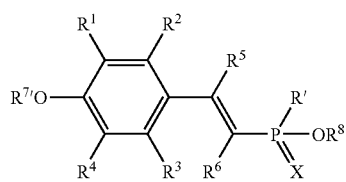

(II)

in which:

X is selected from:
   an oxygen atom and a sulfur atom,

R' is selected from:
   a group S-alkyl, S-aryl, S-amine, S-amide, NH-alkyl, NH-aryl, NH-benzyl, N-(alkyl)$_2$, N-(aryl)$_2$, $R^7$, is selected from:
   H, an alkyl group, an aryl group, said alkyl and aryl groups containing of the order of from 1 to 6 linearly bonded carbon atoms.

Likewise, these fluorophosphonocinnamic compounds of the general formula (I) according to the invention can also be obtained by fluorination of phosphonocinnamic compounds analogous to the compounds of the general formula (II) and corresponding to the general formula:

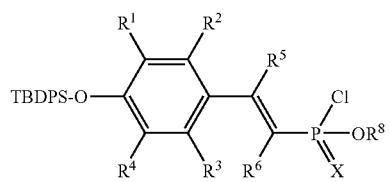

(II')

in which TBDPS denotes a tert-butyldiphenylsilyl group.

The (non-fluorinated) phosphonocinnamic compounds of the general formulae (II) and (II') which can be used as starting products in the process according to the invention are already known in the prior art. Examples of their preparation can be found especially in publications such as Kennedy et al. 1999 (J. Enzyme Inhibition, 14:217-237) and Lapeyre et al., 2003 (Tetrahedron Letters, 44:2445-2447).

According to the invention, in order to fluorinate a phosphonocinnamic compound corresponding to the general formula (II) or (II'), specifically on the phosphorus atom, it is reacted, at a temperature of from −20° C. to 85° C. and advantageously at ambient temperature, with a fluorinating agent comprising a complex formed between a tertiary amine, denoted $R_3N$, and hydrogen fluoride (HF); said tertiary amine ($R_3N$) being substituted by alkyl groups containing of the order of from 1 to 6 linearly bonded carbon atoms.

The invention is accordingly based on the finding that a complex formed between a tertiary amine and hydrogen fluoride constitutes an excellent agent for the fluorination, specifically on the phosphorus atom, of phosphonocinnamic compounds.

Hydrogen fluoride in the form of a complex with a tertiary amine is already known to permit the replacement of a leaving group ad hoc by a fluorine atom (McClinton, 1995, Aldrichimica Acta, 28(2):31-35). In addition, it has been demonstrated that the reactivity, and hence the fluorination capacity, of such complexes is a function of their nucleophilicity. The nucleophilicity is dependent to a large extent on the molar ratio between the tertiary amine and hydrogen fluoride, which can generally be of the order of 1:1, 1:2 or 1:3. A distinction is made between three types of complex denoted $R_3N.HF$, $R_3N.2HF$ and $R_3N.3HF$, which correspond, respectively, to the molar ratios indicated above. The nucleophilicity of these different complexes varies according to the following sequence: $R_3N.2HF > R_3N.3HF > R_3N.HF$.

However, a replacement mediated by such complexes hitherto concerned only leaving groups supposed necessarily to be carried by carbon atoms. For the fluorination of an organo(thio)phosphorus compound at the phosphorus atom, processes such as those described in U.S. Pat. No. 2,962,517 or by Chworos et al., 1999 (Tetrahedron Letters, 40:9337-9340), with the disadvantages arising therefrom, were used predominantly, if not exclusively.

A process according to the invention makes it possible to fluorinate, in a simple manner, specifically the phosphorus atom of organophosphorus compounds of the general formula (II) or (II'), in a single step, with a good yield and total selectivity. A simple step of conventional purification is sufficient to recover the fluorophosphonocinnamic compounds so synthesized.

The process according to the invention additionally has the advantage that it can be carried out using starting products and reagents that are readily obtainable (i.e. either because they are already available commercially and at reasonable cost, or because the method(s) for their synthesis has(have) already been described in the literature) and whose dangerousness is negligible under the normal implementation conditions of a process according to the invention. In particular, the fluorination reaction according to the invention can advantageously be carried out at ambient temperature or at lower temperatures.

As tertiary amine according to the invention there may be mentioned by way of example trimethylamine ($Me_3N$), triethylamine ($Et_3N$), tripropylamine, tributylamine or tripentylamine. Triethylamine ($Et_3N$) is preferably used.

Advantageously and according to the invention, there is used as fluorinating agent a complex of the type $R_3N.HF$, in particular $Et_3N.HF$; that is to say having a molar ratio tertiary amine/hydrogen fluoride of the order of 1:1.

The inventors have also found that, with a complex $R_3N.HF$ (especially with triethylamine as tertiary amine according to the invention) of significantly lower nucleophilicity as compared with complexes of the type $R_3N.2HF$ or $R_3N.3HF$, the complex nevertheless exhibited remarkable reactivity.

Preferably, the reaction is carried out in liquid phase. It is then possible to use a solvent in which the organic compound is soluble, for example dichloromethane, acetonitrile or tetrahydrofuran.

Advantageously and according to the invention, the reaction is carried out with an excess of fluorinating agent. In particular, a molar ratio between the starting compound of formula (II) and the fluorinating agent of the order of from 1.2 to 20 is used. That molar ratio is preferably at least of the order of 5.

Advantageously and according to the invention, the group $R^8$ of a starting phosphonocinnamic compound of the general formula (II) is selected from the leaving groups: $—SCH_2CH_2NHCOCH_3$, $—NHCH_2Ph$ (Ph denotes a phenyl radical).

Advantageously and according to the invention, in the general formula (II) of a starting compound:

$R^{7'}$, denotes a group selected from: $—H$ and $—CH_3$, and
$R^1$ and $R^4$ denote groups selected from: $—H$ and $—OCH_3$.

For example, it is possible to carry out the invention using, as the starting phosphonocinnamic compound corresponding to the general formula (II), one of the phosphonocinnamic thioesters for which a preparation protocol is described in the publication Lapeyre et al., 2003 (Tetrahedron Letters, 44:2445-2447) or an analogous compound. In this example, the leaving group is of the S-amine type, in particular a N-acetylcysteamine radical ($—SCH_2CH_2NHCOCH_3$).

In a very similar manner, it is also possible to carry out the synthesis of the fluorophosphonocinnamic compounds of the general formula (I) according to the invention using phosphonochloridoate compounds of the general formula (II'), especially starting from those which are described as intermediate products of the synthesis reaction of phosphonocinnamic thioesters according to the method of Lapeyre et al., 2003, mentioned above.

As another starting compound corresponding to the general formula (II) there may also be mentioned ethyl-2-N-benzyl-2-(3,4-dimethoxyphenyl)ethane phosphonamide, for which a preparation protocol is described in the publication Kennedy et al., 1999 (J. Enzyme Inhibition, 14:217-237), or an analogous or equivalent compound. In this example, the leaving group is of the secondary amine type, in particular $—NHCH_2Ph$.

The invention relates also, as novel products, to fluorophosphonocinnamic compounds of the general formula (I).

Like a large number of compounds of the cinnamic type, and the non-fluorinated phosphonocinnamic compounds of formula (II) or (II') in particular, the fluorophosphonocinnamic compounds according to the invention exhibit particularly valuable antioxidant activity within the context of a therapeutic or cosmetic treatment for physiological disorders caused by oxidative stress. The work carried out by the inventors has, in fact, demonstrated that the protective effect of the fluorophosphonocinnamic compounds according to the invention against LDL oxidation is advantageously very comparable with that observed with the corresponding non-fluorinated compounds. However, unlike the non-fluorinated compounds, the fluorophosphonocinnamic compounds according to the invention surprisingly also exhibit a protective effect against 4-HNE-related toxicity, very probably because of their fluorine atom.

Owing to their effect of protecting LDLs against oxidation, together with their effect of protecting cells against 4-HNE toxicity, the compounds according to the invention are highly valuable for use in the treatment of atherosclerosis and the cardio- or neuro-vascular complications thereof.

Atherosclerosis is a multifactorial pathology in which lipids play an important role, alongside other genetic or nutritional factors. Among the metabolic factors involved in the initiation and development of plaques, the LDLs (which transport cholesterol from the blood to the peripheral tissues) become atherogenic after oxidative modification in the vascular wall. The oxidation induced in the LDLs provokes in situ the formation of aldehydes (especially 4-HNE), which can in turn oxidize the LDLs. The oxidized LDLs play a major role in the formation of spumous cells, the accumulation of which in fatty striae is the cause of the first atherosclerotic lesions. These oxidized LDLs also have proinflammatory, mitogenic, procoagulant and proapoptotic properties, which may be involved in the evolution of the plaques to more advanced stages or even in phenomena of rupture and thrombosis, which are the cause of cardiovascular accidents.

Molecules capable of blocking the process of LDL oxidation are therefore extremely effective in inhibiting plaque development. Within this context, the invention provides novel agents that block the LDL oxidation pathway and whose effectiveness is all the more remarkable in that they act at least at two different levels of that pathway (direct action on LDLs, and via 4-HNE).

The invention therefore extends also to a cosmetic or therapeutic composition, characterized in that it comprises at least one fluorophosphonocinnamic compound according to the invention, in particular for their effect in blocking the LDL oxidation pathway.

Advantageously and according to the invention, the therapeutic composition is intended for the treatment of physiological disorders caused by oxidative stress, in particular atherosclerosis and the cardio- or neuro-vascular complications thereof. The invention extends also to the use of a fluorophosphonocinnamic compound according to the invention in the preparation of a medicament for the therapeutic treatment of atherosclerosis.

The invention relates also to a method for in vitro protection of LDLs against oxidation, in which LDLs are brought into contact with at least one fluorophosphonocinnamic compound according to the invention.

Advantageously and according to the invention, there may be mentioned as compound according to the invention particularly:

ethyl (E)-2-(4-hydroxy-3-methoxyphenyl)vinyl-phosphonofluoridoate of formula

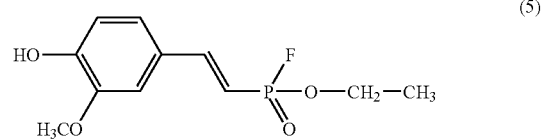

(5)

ethyl
(E)-2-(4-hydroxyphenyl)vinyl-phosphonofluoridoate
of formula

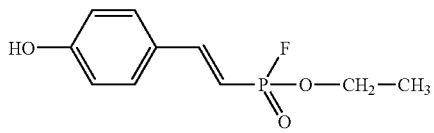
(6)

ethyl (E)-2-(4-hydroxy-3,5-dimethoxyphenyl)vinyl-phosphonofluoridoate of formula

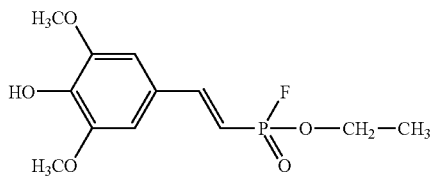
(7)

ethyl (E)-2-(3,4-dimethoxyphenyl)vinyl-phosphonofluoridoate of formula

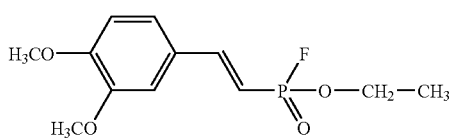
(8)

The invention relates also to a process for the preparation of fluorophosphonocinnamic compounds, to fluorophosphonocinnamic compounds, to a therapeutic composition and to a method for protecting LDLs against oxidation, characterized, in combination, by all or some of the features hereinbefore or hereinafter.

Figure 4:
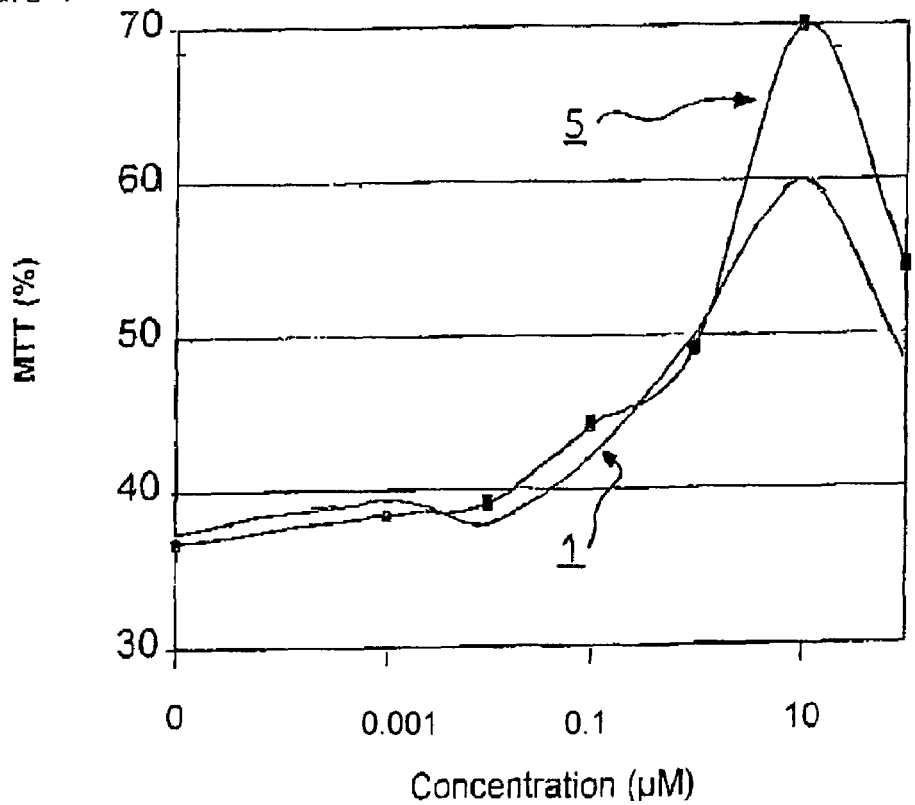

Other objects, features and advantages of the invention will become apparent upon reading the detailed description which follows and which makes reference on the one hand to the synthesis of particular fluorophosphonocinnamic compounds (of formulae denoted 5 to 8) according to the invention and on the other hand to the study of the antiatherogenic biological effect of these compounds. The experimental results make reference especially to the accompanying figures, in which:

FIGS. 1A, 1B and 2 are statistical representations, in bar form, of the overall antioxidant effect of particular compounds according to the invention and of their effect on the protection of cells subjected to oxidative stress, FIGS. 3 and 4 show the progression of the survival of cells in the presence of oxidized LDLs or of 4-HNE, as a function of the concentration in the medium of a particular compound according to the invention.

CHEMICAL SYNTHESIS AND ANALYSIS

Synthesis

1) According to a first procedure, the synthesis of the fluorophosphonocinnamic compounds according to the invention can be carried out with a starting compound of formula (II). The reaction equation is then, diagrammatically, as follows:

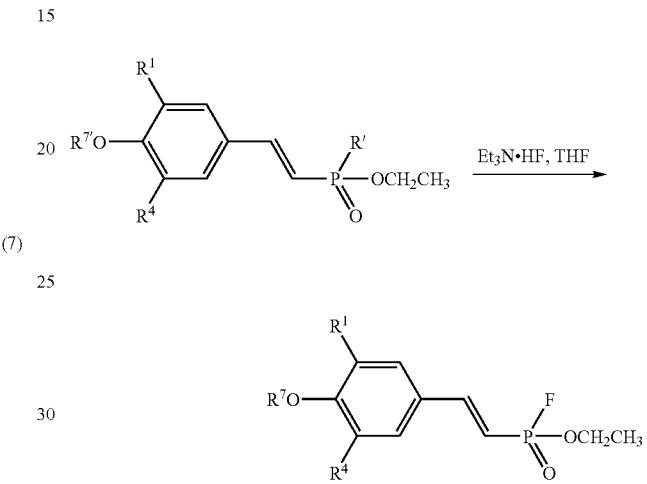

1, $R^1 = R^{7'} = H$, $R^4 = OCH_3$, $R' = S(CH_2)_2NHCOCH_3$
2, $R^1 = R^4 = R^{7'} = H$, $R' = S(CH_2)_2NHCOCH_3$
3, $R^1 = R^4 = OCH_3$, $R^7 = H$, $R' = S(CH_2)_2NHCOCH_3$
4, $R^1 = H = R^4 = OCH_3$, $R^7 = CH_3$, $R' = S(CH_2)_2NHCOCH_3$ }
4', $R^1 = H$, $R^4 = OCH_3$, $R^7 = CH_3$, $R' = NHCH_2Ph$
5, $R^1 = R^7 = H$, $R^4 = OCH_3$
6, $R^1 = R^4 = R^7 = H$
7, $R^1 = R^4 = OCH_3$, $R^7 = H$
8, $R^1 = H$, $R^4 = OCH_3$, $R^7 = CH_3$

The phosphonothioesters designated 1 to 4, in which the leaving group R' is a N-acetyl-cysteamine group, can be synthesized beforehand according to the method described in the publication Lapeyre et al., 2003 (Tetrahedron Letters, 44:2445-2447).

The phosphonamide designated 4', in which the leaving group R' is a secondary amine, can be synthesized beforehand according to the method described in the publication Kennedy et al. 1999 (J. Enzyme Inhibition, 14:217-237).

The triethylamine from Avocado (purity 99%) and the complex $Et_3N.3HF$ from Aldrich (purity 98%) are used to produce the complex $Et_3N.HF$.

The anhydrous tetrahydrofuran (THF) (purity 99.7%) and the ethyl acetate for preparative HPLC (purity 99.8%) are supplied by SDS, France.

2) According to a second procedure, the synthesis of the fluorophosphonocinnamic compounds according to the invention can be carried out starting from a phosphonochloridoate of the general formula (II'). The reaction equation is then, diagrammatically, as follows:

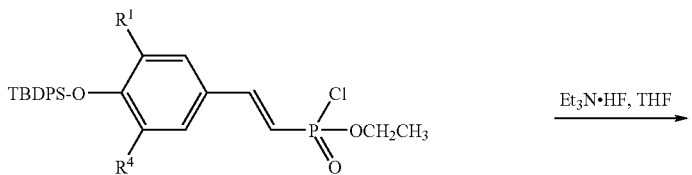

A, $R^1 = H$, $R^4 = OCH_3$ $^{31}P$ NMR (solvent: $D_2O$, 81 MHz, δ ppm): 29.00 (s, P-Cl)
B, $R^1 = R^4 = H$ $^{31}P$ NMR (solvent: $D_2O$, 81 MHz, δ ppm): 30.10 (s, P-Cl)
C, $R^1 = R^4 = OCH_3$ $^{31}P$ NMR (solvent: $D_2O$, 81 MHz, δ ppm): 23.23 (s, P-Cl)

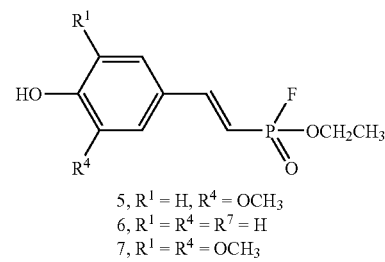

5, $R^1 = H$, $R^4 = OCH_3$
6, $R^1 = R^4 = R^7 = H$
7, $R^1 = R^4 = OCH_3$

These phosphonochloridoate compounds A-C have been described as being intermediate products of the synthesis of the phosphonothioesters 1-4, according to Lapeyre et al., 2003. Within the scope of the invention, these phosphonochloridoate compounds A-C, used as starting materials when carrying out a process according to the invention, can be obtained beforehand quantitatively starting from the corresponding phosphonodiesters according to the method described hereinbelow.

Freshly distilled oxalyl chloride (8.6 mmol) is added at ambient temperature to a solution of silylated phosphonodiester (1.9 mmol) dissolved in 9.7 ml of dichloromethane, placed under nitrogen flux. The reaction mixture is stirred at ambient temperature for 20 hours. The dichloromethane and excess oxalyl chloride are removed under reduced pressure. In order to suppress any trace of oxalyl chloride, a few milliliters of dichloromethane are added and subsequently evaporated off. This operation is repeated three times. The progress of the reaction can be monitored by $^{31}P$ NMR (solvent: $D_2O$, 81 MHz, δ ppm).

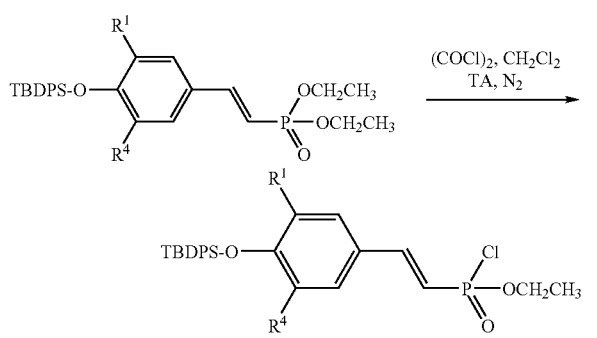

Purification:

The totality of the products is purified by medium-pressure liquid chromatography (MPLC) on silica gel, in a JOBIN-YVON apparatus with axial compression having columns of 20 or 40 mm diameter packed with 15-40 μm silica (MERCK, France), using the appropriate eluant systems.

Analyses:

Thin-layer chromatography is carried out using MERCK 60-$F_{254}$ silica plates.

Melting points were measured using a BÜCHI apparatus.

IR spectra are recorded on a Perkin-Elmer model 1725x FT-IR spectrophotometer with Fourier transform.

Mass spectra (chemical ionization DCI or electronic impact EI) are carried out on a NERMAG R10-10 quadripolar spectrometer.

Ultraviolet spectra are recorded on a HEWLETT PACKARD 8453 instrument.

NMR spectra are recorded on BRÜCKER apparatuses:

AC-250 working at 250 MHz for the $^1H$ nucleus, at 62.5 MHz for the $^{13}C$ nucleus;

AC-200 working at 81 MHz for the $^{31}P$ nucleus, 188.5 MHz for the $^{19}F$ nucleus.

Chemical shifts (δ) are expressed in ppm, taking the tetramethylsilane signal as reference for the $^1H$ and $^{13}C$ nuclei, the phosphoric acid signal as reference for the $^{31}P$ nucleus and the hydrofluoric acid signal as reference for the $^{19}F$ nucleus. The coupling constants J are expressed in hertz and the multiplicity of the signals is indicated by a small letter: s (singlet), d (doublet), t (triplet), q (quadruplet), m (multiplet).

Synthesis examples using a phosphonothioester as starting product:

1/Ethyl (E)-2-(4-hydroxy-3-methoxyphenyl)vinyl-phosphonofluoridoate a) Synthesis Protocol:

The silylated phosphonothioester 1 (0.64 mmol) is dissolved in 4 ml of THF, under nitrogen, in a 25 ml two-necked flask. 2.1 mmol of triethylamine and then 1.1 mmol of the complex $Et_3N.3HF$ are then added using a microsyringe. The solution so obtained is stirred at 20° C. for 2 hours. The crude reaction mixture is concentrated under reduced pressure and then the compound 5 so obtained is purified by MPLC (eluant AcOEt).

b) Characterization:

Appearance: white solid

Yield 64% $R_f$: 0.67 (AcOEt) M.p.: 92-93° C. IR: (KBr flakes, CHCl$_3$) ν (3242 cm$^{-1}$, O—H), ν (3006 cm$^{-1}$, C—H alkene), ν (1617 cm$^{-1}$, C=C aromatic), ν (1598, 1516 cm$^{-1}$, C=C aromatic), ν (1271 cm$^{-1}$, P=O), ν (1162 cm$^{-1}$, P—O—C), δ (982 cm$^{-1}$, C=C trans), δ (881, 800 cm$^{-1}$, aromatic), δ (756 cm$^{-1}$, P—O—R) Mass: MS (CI NH$_3$, MNH$_4^+$) 278 UV: (Na$_2$HPO$_4$/KH$_2$PO$_4$, 100 mM pH 6.25) λ=313 nm, ε=18400 mol$^{-1}$.l.cm$^{-1}$ $^1$H NMR (solvent: CDCl$_3$, 250 MHz, δ ppm): 1.38 (t, 3H, $^3J_{H-H}$=7.1 Hz, C$\underline{H}_3$CH$_2$), 3.87 (s, 3H, CH$_3$O), 4.27 (qd, 2H, $^3J_{H-H}$=$^3J_{P-O-C\underline{H}}$=7.1 Hz, CH$_2$O), 6.04 (dd, 1H, $^3J_{H-H}$=17.5 Hz, $^2J_{P-C\underline{H}}$=19.6 Hz, C=C$\underline{H}$—P), 6.92 (m, 4H, OH+H$_6$+H$_2$+H$_5$), 7.51 (dd, 1H, $^3J_{H-H}$=17.5 Hz, $^3J_{P-CH=C\underline{H}}$=24.7 Hz, C$\underline{H}$=CH—P) $^{13}$C NMR (solvent: CDCl$_3$, 62.5 MHz, δ ppm): 17.38 (d, 1C, $^3J_{C-P}$=6.0 Hz, $\underline{C}$H$_3$CH$_2$), 56.98 (s, 1C, CH$_3$O), 64.58 (d, 1C, $^2J_{C-P}$=6.0 Hz, CH$_2$O), 106.81 (dd, 1C, $^1J_{C-P}$=207.3 Hz, $^2J_{C-F}$=32.4 Hz, C=$\underline{C}$—P), 110.60 (s, 1C, C$_6$), 116.09 (s, 1C, C$_5$), 124.16 (s, 1C, C$_2$), 127.45 (d, 1C, $^3J_{C-P}$=26.2 Hz, C$_1$), 148.26 (s, 1C, C$_4$), 150.08 (s, 1C, C$_3$), 152.85 (dd, 1C, $^2J_{C-P}$=7.9 Hz, $^3J_{C-F}$=3.9 Hz, $\underline{C}$=C—P) $^{31}$P NMR (solvent: CDCl$_3$, 81 MHz, δ ppm): 19.79 (d, $^3J_{P-F}$=1023 Hz, P—F) $^{19}$F NMR (solvent: CDCl$_3$, 188.3 MHz, δ ppm): 11.75 (d, $^3J_{F-P}$=1023 Hz, F—P) Elemental analyses (theoretical/experimental): carbon (50.78/50.93) hydrogen (5.42/5.36)

2/Ethyl (E)-2-(4-hydroxyphenyl)vinyl-phosphonofluoridoate a) Synthesis Protocol:

The phosphonothioester 2 (0.64 mmol) is dissolved in 4 ml of THF, under nitrogen, in a 25 ml two-necked flask. 2.1 mmol of triethylamine and then 1.1 mmol of the complex Et$_3$N.3HF are then added using a microsyringe. The solution so obtained is stirred at 20° C. for 3 hours. The crude reaction mixture is concentrated under reduced pressure and then the compound 6 so obtained is purified by MPLC (eluant AcOEt).

b) Characterization:

Appearance: transparent oil

Yield: 66% $R_f$: 0.64 (AcOEt) IR: (KBr flakes, CHCl$_3$) ν (3233 cm$^{-1}$, O—H), ν (3020 cm$^{-1}$, C—H alkene), ν (1604 cm$^{-1}$, C=C), ν (1585, 1515 cm$^{-1}$, C=C), ν (1230 cm$^{-1}$, P=O), ν (1170 cm$^{-1}$, P—O—C), δ (984 cm$^{-1}$, C=C trans), δ (843 cm$^{-1}$, aromatic), δ (757 cm$^{-1}$, P—O—C) Mass: MS (CI NH$_3$, MNH$_4^+$) 248 UV: (Na$_2$HPO$_4$/KH$_2$PO$_4$, 100 mM pH 6.25) λ=285 nm, ε=21200 mol$^{-1}$.l.cm$^{-1}$ $^1$H NMR (solvent: CDCl$_3$, 250 MHz, δ ppm): 1.41 (t, 3H, $^3J_{H-H}$=7.0 Hz, C$\underline{H}_3$CH$_2$), 4.30 (qd, 2H, $^3J_{H-H}$=$^3J_{P-O-C\underline{H}}$=7.0 Hz, CH$_2$O), 6.03 (dd, 1H, $^3J_{H-H}$=17.5 Hz, $^2J_{P-C\underline{H}}$=20.4 Hz, C=C$\underline{H}$—P), 6.92 (d, 2H, $^3J_{H-H}$=8.7 Hz, H$_2$+H$_6$), 7.37 (d, 2H, $^3J_{H-H}$=8.7 Hz, H$_3$+H$_5$), 7.54 (dd, 1H, $^3J_{H-H}$=17.5 Hz, $^3J_{P-CH=C\underline{H}}$=25.0 Hz, C$\underline{H}$=CH—P), 8.54 (s, 1H, OH) $^{13}$C NMR (solvent: CDCl$_3$, 62.5 MHz, δ ppm): 17.41 (d, 1C, $^3J_{C-P}$=6.0 Hz, $\underline{C}$H$_3$CH$_2$), 65.00 (d, 1C, $^2J_{C-P}$=6.2 Hz, CH$_2$O), 105.50 (dd, 1C, $^1J_{C-P}$=208.4 Hz, $^2J_{C-F}$=31.5 Hz, C=$\underline{C}$—P), 117.29 (s, 2C, C$_2$+C$_6$), 126.88 (d, 1C, $^3J_{C-P}$=25.7 Hz, C$_1$), 131.28 (s, 2C, C$_3$+C$_5$), 153.33 (dd, 1C, $^2J_{C-P}$=7.8 Hz, $^3J_{C-F}$=4.7 Hz, $\underline{C}$=C—P), 161.12 (s, 1C, C$_4$) $^{31}$P NMR (solvent: CDCl$_3$, 81 MHz, δ ppm): 20.53 (d, $^3J_{P-F}$=1024 Hz, P—F) $^{19}$F NMR (solvent: CDCl$_3$, 188.3 MHz, δ ppm): 11.17 (d, $^3J_{F-P}$=1024 Hz, F—P)

3/Ethyl (E)-2-(4-hydroxy-3,5-dimethoxyphenyl) vinyl-phosphonofluoridoate a) Synthesis Protocol:

The phosphonothioester 3 (0.64 mmol) is dissolved in 4 ml of THF, under nitrogen, in a 25 ml two-necked flask. 2.1 mmol of triethylamine and then 1.1 mmol of the complex Et$_3$N.3HF are then added using a microsyringe. The solution so obtained is stirred at 20° C. for 3 hours. The crude reaction mixture is concentrated under reduced pressure and then the compound 7 so obtained is purified by MPLC (eluant AcOEt).

b) Characterization:

Appearance: white solid

Yield: 68% $R_f$: 0.59 (AcOEt) M.p.: 153-155° C. IR: (KBr flakes, CHCl$_3$) ν (3255 cm$^{-1}$, O—H), ν (3019 cm$^{-1}$, C—H alkene), ν (1618 cm$^{-1}$, C=C aromatic), ν (1597, 1513 cm$^{-1}$, C=C aromatic), ν (1251 cm$^{-1}$, P=O), ν (1158 cm$^{-1}$, P—O—C), δ (975 cm$^{-1}$, C=C trans), ν (752 cm$^{-1}$, P—O—R) Mass: MS (CI NH$_3$, MNH$_4^+$) 308 UV: Na$_2$HPO$_4$/KH$_2$PO$_4$, 100 mM pH 6.25) λ=310 nm, ε=18000 mol$^{-1}$.l.cm$^{-1}$ $^1$H NMR (solvent: CDCl$_3$, 250 MHz, δ ppm): 1.40 (t, 3H, J$_{H-H}$=7.0 Hz, C$\underline{H}_3$CH$_2$), 3.90 (s, 6H, CH$_3$O), 4.29 (qd, 2H, $^3J_{H-H}$=$^3J_{P-O-C\underline{H}}$=7.0 Hz, CH$_2$O), 6.00 (s, 1H, OH), 6.08 (dd, 1H, $^3J_{H-H}$=17.5 Hz, $^2J_{P-C\underline{H}}$=19.2 Hz, C=C$\underline{H}$—P), 6.73 (d, 2H, H$_2$+H$_6$), 7.50 (dd, 1H, $^3J_{H-H}$=17.5 Hz, $^3J_{P-CH=C\underline{H}}$=24.5 Hz, C$\underline{H}$=CH—P) $^{13}$C NMR (solvent: CDCl$_3$, 62.5 MHz, δ ppm): 17.45 (d, 1C, $^3J_{C-P}$=6.0 Hz, $\underline{C}$H$_3$CH$_2$), 57.44 (s, 2C, CH$_3$O), 64.54 (d, 1C, $^2J_{C-P}$=6.0 Hz, CH$_2$O), 106.12 (s, 2C, C$_2$+C$_6$), 107.81 (dd, 1C, $^1J_{C-P}$=207.0 Hz, $^2J_{C-F}$=32.9 Hz, C=$\underline{C}$—P), 126.60 (d, 1C, $^3J_{C-P}$=26.2 Hz, C$_1$), 138.88 (s, 2C, C$_3$+C$_5$), 148.39 (s, 1C, C$_4$), 152.82 (dd, 1C, $^2J_{C-P}$=7.9 Hz, $^3J_{C-F}$=4.2 Hz, $\underline{C}$=C—P) $^{31}$P NMR (solvent: CDCl$_3$, 81 MHz, δ ppm): 19.43 (d, $^3J_{P-F}$=1023 Hz, P—F) $^{19}$F NMR (solvent: CDCl$_3$, 188.3 MHz, δ ppm): 11.90 (d, $^3J_{F-P}$=1023 Hz, F—P) Elemental analyses (theoretical/experimental): carbon (49.66/49.60) hydrogen (5.53/5.37)

4/Ethyl (E)-2-(3,4-dimethoxyphenyl)vinyl-phosphonofluoridoate a) Synthesis Protocol:

The phosphonothioester 4 (0.64 mmol) is dissolved in 4 ml of THF, under nitrogen, in a 25 ml two-necked flask. 2.1 mmol of triethylamine and then 1.1 mmol of the complex Et$_3$N.3HF are then added using a microsyringe. The solution so obtained is stirred at 20° C. for 2 hours. The crude reaction mixture is concentrated under reduced pressure and then the compound 8 so obtained is purified by MPLC (eluant AcOEt).

b) Characterization:

Appearance: transparent oil

Yield: 69% $R_f$: 0.59 (AcOEt) IR: (KBr flakes, CHCl$_3$) ν (3019 cm$^{-1}$, C—H alkene), ν (2938 cm$^{-1}$, C—H alkane), ν (1616 cm$^{-1}$, C=C), ν (1583, 1514 cm$^{-1}$, C=C), ν (1270 cm$^{-1}$, P=O), ν (1160 cm$^{-1}$, P—O—C), δ (981 cm$^{-1}$, C=C trans), δ (880, 852 cm$^{-1}$, aromatic), δ (757 cm$^{-1}$, P—O—R) Mass: MS (CI, MH$^+$) 275 UV: (Na$_2$HPO$_4$/KH$_2$PO$_4$, 100 mM pH 6.25) λ=312 nm, ε=2500 mol$^{-1}$.l.cm$^{-1}$ $^1$H NMR (solvent: CDCl$_3$, 250 MHz, δ ppm): 1.42 (t, 3H, $^3J_{H-H}$=7.0 Hz, C$\underline{H}_3$CH$_2$), 3.92 (s, 6H, CH$_3$O), 4.30 (qd, 2H, $^3J_{H-H}$=$^3J_{P-O-C\underline{H}}$=7.0 Hz, CH$_2$O), 6.09 (dd, 1H, J$_{H-H}$=$^2J_{P-C\underline{H}}$=18.4 Hz, C=C$\underline{H}$—P), 6.88 (d, 1H, J$_{H-H}$=8.2 Hz, H$_6$), 7.03 (s, 1H, H$_2$), 7.10 (d, 1H, $^2J_{H-H}$=8.2 Hz, H$_5$), 7.56 (dd, 1H, $^3J_{H-H}$=17.4 Hz, $^3J_{P-CH=C\underline{H}}$=24.4 Hz, C$\underline{H}$=CH—P) $^{13}$C NMR (solvent: CDCl$_3$, 62.5 MHz, δ ppm): 16.34 (d, 1C, $^3J_{C-P}$=6.0 Hz, $\underline{C}$H$_3$CH$_2$), 55.94, 56.02 (s, 2C, CH$_3$O), 63.38 (d, 1C, $^2J_{C-P}$ =6.8 Hz, $CH_2O$), 106.85 (dd, 1C, $J_{C-P}$=206.9 Hz, $^2J_{C-F}$=33.2 Hz, C=$\underline{C}$—P), 109.51 (s, 1C, $C_6$), 111.03 (s, 1C, $C_2$), 122.75 (s, 1C, $C_5$), 149.34 (s, 1C, $C_1$), 151.32 (dd, 1C, $^2J_{C-P}$=8.3 Hz, $^3J_{C-F}$=4.5 Hz, $\underline{C}$=C—P), 151.73 (s, 2C, $C_4$+$C_3$) $^{31}$P NMR (solvent: $CDCl_3$, 81 MHz, δ ppm): 19.49 (d, $^3J_{P-F}$=1024 Hz, P—F) $^{19}$F NMR (solvent: $CDCl_3$, 188.3 MHz, δ ppm): 11.92 (d, $^3J_{F-P}$=1024 Hz, F—P)

c) Observation:

According to another method for synthesis of the compound 8, as starting compound, it is also possible to use (E)-ethyl-2-N-benzyl-2-(3,4-dimethoxyphenyl)ethene phosphonamide.

Synthesis example using the phosphonochloridoate C as starting product:

Once the phosphonochloridoate C has been prepared, it (0.42 mmol; 1 eq.) is dissolved, under an inert atmosphere, in 4 ml of freshly distilled THF. Triethylamine (197 μl; 139 mmol; 3.33 eq.) and the complex $Et_3N.3HF$ (112 μl; 0.69 mmol; 1.67 eq.) are added. The reaction medium is stirred magnetically at ambient temperature for 30 minutes. The progress of the reaction is monitored by $^{31}$P NMR. The reaction is stopped by addition of AcOEt. The precipitate obtained is filtered over BÜCHNER and then the filtrate is hydrolysed. The aqueous phase is extracted three times using AcOEt.

The organic phases are combined, dried over anhydrous $Na_2SO_4$ and then concentrated in vacuo.

b) Characterization:

Appearance: white powder

Yield: 77% $R_f$: 0.23 (AcOEt/EP 4/6) M.p.: 69-70° C. IR: (KBr flakes, $CHCl_3$) ν (3233 cm$^{-1}$, O—H), ν (3020 cm$^{-1}$, C—H alkene), ν (1604 cm$^{-1}$, C=C), ν (1585 cm$^{-1}$, C=C), ν (1230 cm$^{-1}$, P=O), ν (1170 cm$^{-1}$, P—O—C), δ (985 cm$^{-1}$, C=C trans), ν (843 cm$^{-1}$, C=C aromatic) Mass: MS (CI $NH_3$, $MNH_4^+$) 308 UV: ($Na_2HPO_4$/$KH_2PO_4$, 100 mM pH 6.25) λ=310 nm, ε=18000 mol$^{-1}$.l.cm$^{-1}$ $^1$H NMR (solvent: $CDCl_3$, 250 MHz, δ ppm): 1.38 (t, 3H, $J_{H-H}$=7.0 Hz, C$\underline{H}_3CH_2$), 3.88 (s, 6H, $CH_3O$), 4.27 (qd, 2H, $^3J_{H-H}$=$^3J_{H-H}$=7.0 Hz, $^3J_{H-P}$=7.0 Hz, $CH_3CH_2O$), 5.81 (s, 1H, OH), 6.07 (dd, 1H, $^3J_{H-H}$=17.5 Hz, $^2J_{H-P}$=19.2 Hz, CH=C$\underline{H}$—P), 6.72 (s, 2H, $H_2$+$H_6$), 7.49 (dd, 1H, $3J_{H-H}$=17.5 Hz, $^3J_{H-P}$=24.5 Hz, C$\underline{H}$=CH—P) $^{13}$C NMR (solvent: $CDCl_3$, 62.5 MHz, δ ppm): 16.30 (d, 1C, $^3J_{C-P}$=6.0 Hz, $\underline{C}H_3CH_2O$), 56.35 (s, 2C, $CH_3O$), 63.41 (d, 1C, $^2J_{C-P}$=6.0 Hz, $CH_3\underline{C}H_2O$), 105.11 (s, 2C, $C_2$+$C_6$), 106.75 (dd, 1C, $^1J_{C-P}$=207.0 Hz, $^2J_{C-F}$=33.0 Hz, C=$\underline{C}$—P), 125.50 (d, 1C, $^3J_{C-P}$=25.5 Hz, $C_1$), 137.86 (s, 1C, $C_4$), 147.32 (s, 2C, $C_3$+$C_5$), 151.62 (dd, 1C, $^2J_{C-P}$=7.5 Hz, $^3J_{C-F}$=3.8 Hz, $\underline{C}$=C—P) $^{31}$P NMR (solvent: $CDCl_3$, 81 MHz, δ ppm): 19.50 (d, $^1J_{P-F}$=1023 Hz, P—F) $^{19}$F NMR (solvent: $CDCl_3$, 188.3 MHz, δ ppm): 11.88 (d, $^1J_{F-P}$=1023 Hz, F—P) MS (IC, $NH_3$) m/z: 248 ($MNH_4^+$, 100%), 291 ($MH^+$, 38%) Elemental analyses (theoretical/experimental): carbon (70.13/70.00) hydrogen (7.65/7.71)

Antiatherogenic Effect of the Synthesized Compounds

1/Study of the Effect In Vitro of the Synthesized Compounds with Regard to LDL Oxidation Natural LDLs from serum pools obtained from healthy subjects are purified by preparative ultracentrifugation with a KBr gradient. The LDLs are then dialysed in an isotonic NaCl buffer (9 g/l, pH 7.2) in order to remove the KBr and are then sterilised (0.2 nm filter) and stored under nitrogen until used (maximum: 2 weeks).

Human endothelial cells in culture (HMEC or ECV304 lines) are cultivated in multi-well dishes and brought to subconfluence in RPMI 1460 culture medium containing 10% fetal calf serum and antibiotics (penicillin, streptomycin).

The standard culture medium is replaced by RPMI 1640 (1 ml/well) containing 1 μM of $CuSO_4$ (in order to initiate oxidation) and 100 μg/ml of natural LDLs, as well as the various test compounds (denoted 5 to 8) in variable concentrations. After 6 hours' contact, a portion of the medium is removed for measurement of the LDL oxidation parameters (TBARS). After 24 hours' contact, the residual viability of the cells in contact with the oxidized LDLs (optionally protected against oxidation by the CPSs) is measured (MTT test).

The LDLs are oxidized rapidly by the vascular cells in culture. Preliminary studies have shown that this oxidation requires the presence of heavy metals (such as copper or iron), hence the addition of $CuSO_4$. The oxidation kinetics is slowed at the beginning by the endogenous antioxidants (vitamin E) and continues for more than 24 hours (plateau). The oxidation of the LDLs is measured after 6 hours' contact because it is then in the exponential phase and the possible protective effect of the antioxidants is more noticeable. The oxidation is measured by analyzing the TBARS (substances reactive to thiobarbituric acid), permitting an overall, quantitative and sensitive analysis of the oxidation phenomenon.

The compounds synthesized beforehand, denoted 5 to 8, respectively, are dissolved in DMSO and tested at concentrations varying from 0.1 to 100 μM (final concentration of DMSO not exceeding 0.05%). No autotoxicity of compounds 5 to 8 has been observed on the cells at the concentrations used in this study (results not given).

The results, given in FIG. 1A, show an antioxidant effect for each of compounds 5 to 8, although the antioxidant effect is much more marked for compound 5 with significant protection against LDL oxidation at 1 μM and above, which increases at higher concentrations.

In FIG. 1A, the results are expressed as a percentage of the control (test without synthesized compound with the oxidized LDLs alone). The level of TBARS in the LDLs oxidized by the cells in 6 hours is from 6 to 10 nmoles of TBARS/mg of apoB. Compounds 5 to 8 are added at concentrations varying from 0.1 to 100 μM. The results given correspond to the average of three separate experiments carried out in duplicate.

The oxidized LDLs are toxic for the vascular cells in culture. This toxic effect can be studied by the MTT colorimetric test, which measures cell viability. The results, given in FIG. 1B, show a residual viability of from 15 to 20% for the cells in contact for 24 hours with the oxidized LDLs alone (in the absence of compounds 5 to 8). In correlation with the effect on the TBARS, compound 5 is found to be very effective at preventing the toxicity of the LDLs oxidized by the cells, as a function of the dose used. The other compounds have a more limited effect.

Compound 5 is very effective at protecting the LDLs against oxidation by the vascular cells and their resulting toxicity is limited. This effect is comparable with that observed with polyphenols such as catechol or quercetin, with an effect that is less toxic (for the cells) at concentrations equal to or greater than 100 μM.

2/In Vitro Study of the Cytoprotective Effect of Compound 5 with Regard to Oxidized LDLs We have studied the cytoprotective effect of compound 5 on the toxicity of LDLs already oxidized in the absence of any other synthesized compound (6 to 8) or antioxidant agents. These oxidized LDLs are toxic for the endothelial cells (toxicity evaluated by the MTT test). ECV304 cells are incubated with LDLs oxidized by UV irradiation (200 μg/ml) for 24 hours, in the absence (0) or in the presence of compound 5 (concentrations from 0.1 to 100 μM). Finally, the MTT test is carried out. The results are expressed as a percentage of the negative control (incubated in the absence of LDLs and of compound 5). The results given correspond to the average of three separate experiments carried out in duplicate.

As shown in FIG. 2, increasing doses of compound 5 effectively protect against the toxicity of oxidized LDLs in the ECV304 endothelial cells, which suggests that compound 5 has both an antioxidant and a cytoprotective effect.

3/Comparative In Vitro Study of the Effects of Compounds 5 and 1 (Same Structure as Compound 5 without the Fluorinated Group)

The antioxidant/carbonyl-trapping effect might be increased by the fluorine atom. In order to confirm this hypothesis, we have studied the antioxidant and cytoprotective effect of compound 1, the chemical structure of which is identical to that of compound 5 except for the absence of the fluorine atom.

This effect of compounds 1 and 5 has been studied on the one hand on the oxidation of LDLs by the ECV304 cells, and their resulting toxicity.

To this end, the ECV304 cells are incubated for 6 hours with natural LDLs (100 μg/ml) in the presence of $CuSO_4$ (1 μM) and variable concentrations of compound 1 or of compound 5. The medium is then recovered, an aliquot is removed in order to analyze the TBARS, and the remainder of the medium is re-incubated with other ECV304 cells in order to study the toxic effect. The level of TBARS in the control (LDLs alone) is 7.5 nmol/mg apoB. The results obtained are given in Table 1 below and correspond to the average of 4 separate experiments carried out in duplicate.

The results obtained show that the effect against oxidation of LDLs and their resulting toxicity is comparable between compound 1 and compound 5. This effect is therefore linked in principle with the presence of the phenol group on the two molecules.

TABLE 1

| Concentration (μM) | | TBARS (%) | MTT (%) |
| --- | --- | --- | --- |
| Control (LDLs alone) | | 100 | 25 ± 5 |
| Compound 1 | 0.1 | 102 ± 5 | 23 |
| | 1 | 47 ± 5 | 49 |
| | 10 | 23 ± 5 | 85 |
| | 100 | 8 ± 5 | 105 |
| Compound 5 | 0.1 | 100 ± 5 | 24 |
| | 1 | 51 ± 5 | 52 |
| | 10 | 24 ± 5 | 90 |
| | 100 | 7 ± 5 | 104 |

On the other hand, the effect of compounds 1 and 5 was also compared at the level of their cytoprotective effect with regard to oxidized LDLs and 4-HNE.

To this end, the endothelial cells are incubated with 200 μg/ml of oxidized LDLs or 25 μM of 4-HNE and increasing concentrations of compounds 1 or 5. The toxicity is evaluated after 24 hours by an MTT test.

FIG. 3 shows the results obtained in the tests carried out with oxidized LDLs; the results are expressed as a percentage of the unstimulated control.

FIG. 4 shows the results obtained in the tests carried out with 4-HNE. The protective effect of the synthesized compounds on the toxicity induced by 4-HNE is linked solely with the carbonyl-trapping effect. It will be noted from these results that only compound 5 is effective, beyond the relatively weak concentrations (1 μM), and persists at higher concentrations, while compound 1 is ineffective and even toxic at higher doses. These results therefore show that compound 5 has a carbonyl-trapping effect linked with the fluorine group, which permits effective protection against aldehyde-induced toxicity.

The totality of these results shows that the cytotoxicity of the oxidized LDLs is not simply linked with the presence of carbonyl groups, and that oxidizing stress is also involved. This explains why a much more valuable protective effect is obtained with compound 5 than with the non-fluorinated compound 1.

3/In Vivo Validation of the Anti-Atherogenic Effect of the Fluorophosphonocinnamic Compounds According to the Invention The potentially antiatherogenic effect of the fluorophosphonocinnamic compounds according to the invention, in particular compound 7, was likewise studied on an animal model of atherosclerosis represented by apoE$^{-/-}$ mice.

a) Description of the Animal Model and Experimental Protocol apoE knock-out mice are mice that are deficient in apoprotein E (apoE), which induces an accumulation of plasmatic cholesterol associated with an increase in the level of LDLs and IDLs (intermediate-density lipoproteins) and a reduction in the level of plasmatic HDL. These mice represent a conventional model for the study of the development of atherosclerotic plaques (accumulation of fatty striae which form the primary lesions) and of molecules capable of slowing down or blocking the formation of these lesions. These mice spontaneously develop atherosclerotic plaques (without a hyperlipidic diet).

The 4-week-old weaned mice are divided into 2 groups of 13 animals, fed with a standard diet.

Group 1 (treated) receives 10 mg/kg of compound 7 in the drinking water, compound 7 having previously been dissolved in ethanol and then diluted in water to give a final concentration of compound 7 of 30 mg/l, and in 0.05% ethanol).

Group 2 (control) receives drinking water containing 0.05% ethanol. The concentration of compound 7 has been calculated based on a volume of water of from 6 to 10 ml/day and per mouse weighing 30 g.

Compound 7 is stable at ambient temperature for 4 days (stability verified by HPLC). The drinking bottles are changed twice per week.

The total treatment time is 4 months.

After 4 months, the animals are sacrificed and the hearts are washed in a PBS (phosphate buffered saline) buffer, frozen (Tissue TeK) and stored at −80° C. Analysis of the atherosclerotic lesions is effected at the level of the aortic sinus, on sections 10 μm thick stained with a lipid-specific dye (oil red O) and counter-stained with hematoxylin/eosin, and then the surface area is measured by morphometric evaluation of the size of the lesions (Biocom morphometry system, Cyberview 3.0 software). The average surface area of the lesions, expressed in μm$^2$, is used to evaluate the size of the lesions in each animal.

b) Results

The protective effect of compound 7 is tested on 4-week-old apoE$^{-/-}$ mice. At this stage, the development of atherosclerotic lesions is minor, therefore the addition of potentially antiatherogenic compounds slows down the spontaneous development of plaques. The lesions are analyzed at the level of the aortic sinus after 4 months' treatment (or not), because at this stage the lesions at the level of the ascending part of the aorta are still not very developed. The corresponding numerical results obtained are indicated in Table 2 below.

TABLE 2

|  | S1<br>Surface area of the aortic<br>sinus (μm²) | S2<br>Surface area of the aortic<br>sinus (μm²) + compound 7 |
| --- | --- | --- |
|  | 11436 | 15012 |
|  | 20137 | 9886 |
|  | 26525 | 17441 |
|  | 11526 | 18430 |
|  | 26714 | 16651 |
|  | 17042 | 21429 |
|  | 14278 | 21710 |
|  | 14218 | 8274 |
|  | 28196 | 8539 |
|  | 24633 | 11266 |
|  | 23457 | 15381 |
|  | 22647 | 10310 |
|  | 21423 | 18774 |
| Average | 20171.6923 | 14854.0769 |
| Standard deviation | 5663.5393 | 4557.2625 |
|  | S2/S1 = 0.73 | |

The study shows that adding compound 7 to the drinking water brings about a substantial reduction in the surface area of the atherosclerotic plaques at the level of the aortic sinus (reduction of 27% on average relative to the surface area of the untreated control animals, with a large standard deviation but comparable in the two populations).

The invention claimed is:

1. A process for the synthesis of a fluorophosphonocinnamic compound of the general formula

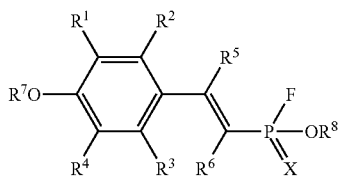

(I)

X being selected from the group consisting of:
an oxygen atom and a sulfur atom,
$R^1$, $R^2$, $R^3$, $R^4$, $R^5$ and $R^6$ being selected from the group consisting of:
H, an alkyl group, an aryl group, OH, O-alkyl, S-alkyl, $NH_2$, NH-alkyl, and N-(alkyl)$_2$,
$R^7$ being selected from the group consisting of:
H, an alkyl group, an aryl group, and a silyl group,
$R^8$ being selected from the group consisting of:
H, an alkyl group, and an aryl group,
said alkyl and aryl groups containing from 1 to 6 linearly bonded carbon atoms, comprising:
fluorinating a phosphonocinnamic compound of the general formula:

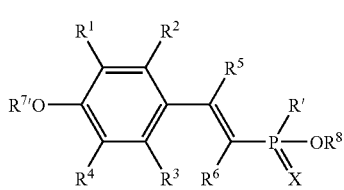

(II)

X being selected from the group consisting of:
an oxygen atom and a sulfur atom,
R' being selected from the group consisting of:
a group S-alkyl, S-aryl, S-amine, S-amide, NH-alkyl, NH-aryl, N-(alkyl)$_2$, and N-(aryl)$_2$,
$R^7$, being selected from the group consisting of:
H, an alkyl group, and an aryl group,
said alkyl and aryl groups containing from 1 to 6 linearly bonded carbon atoms,
or of a phosphonocinnamic compound of the general formula:

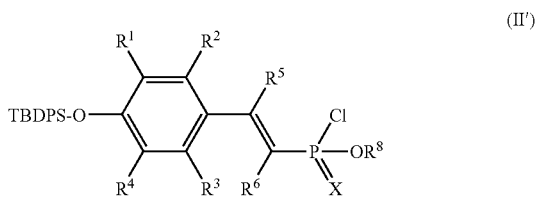

(II')

TBDPS denoting a tert-butyldiphenylsilyl group,
by reacting the phosphonocinnamic compound, at a temperature of from −20° C. to 85° C., with at least one fluorinating agent comprising a complex formed between a tertiary amine, denoted $R_3N$, and hydrogen fluoride; said tertiary amine being substituted by alkyl groups containing from 1 to 6 linearly bonded carbon atoms.

2. The process as claimed in claim 1, wherein said tertiary amine is triethylamine, $Et_3N$.

3. The process as claimed in claim 1, wherein there is used as the fluorinating agent a complex having a molar ratio of tertiary amine/hydrogen fluoride of 1:1, denoted $R_3N.HF$.

4. The process as claimed in claim 1, wherein the reaction is carried out in liquid phase in a solvent in which the phosphonocinnamic compound of formula (II) is soluble.

5. The process as claimed in claim 4, wherein there is used a solvent selected from the group consisting of: dichloromethane, acetonitrile, and tetrahydrofuran.

6. The process as claimed in claim 1, wherein the reaction is carried out with a molar ratio between the phosphonocinnamic compound of formula (II) and the fluorinating agent from 1.2 to 20.

7. The process as claimed in claim 1, wherein the group $R^8$ of a phosphonocinnamic compound of the general formula (II) is —$SCH_2CH_2NHCOCH_3$ or —$NHCH_2Ph$.

8. The process as claimed in claim 1, wherein in the starting phosphonocinnamic compound of the general formula (II):
R denotes a group selected from: —H and —$CH_3$, and
$R^1$ and $R^2$ denote groups selected from: —H and —$OCH_3$.

9. A fluorophosphonocinnamic compound of the general formula:

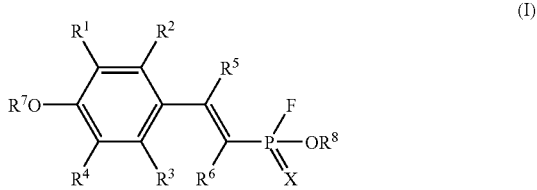

(I)

X being selected from:
an oxygen atom and a sulfur atom,
$R^1$, $R^2$, $R^3$, $R^4$, $R^5$ and $R^6$ being selected from the group consisting of: H, an alkyl group, an aryl group, OH, O-alkyl, S-alkyl, $NH_2$, NH-alkyl, and N-(alkyl)$_2$;
$R^7$ being selected from the group consisting of:
H, an alkyl group, an aryl group, and a silyl group;
$R^8$ being selected from the group consisting of:
H, an alkyl group, and an aryl group,
said alkyl and aryl groups containing from 1 to 6 linearly bonded carbon atoms.

10. A compound as claimed in claim 9, wherein the compound is ethyl (E)-2-(4-hydroxy-3-methoxyphenyl)vinyl-phosphonofluoridoate of formula:

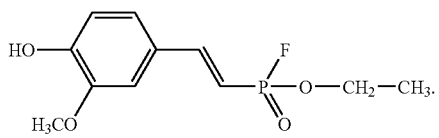

(5)

11. A compound as claimed in claim 9, wherein the compound is ethyl (E)-2-(4-hydroxyphenyl)vinyl-phosphonofluoridoate of formula:

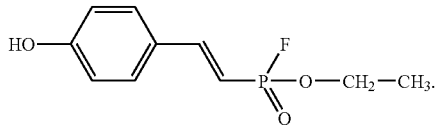

(6)

12. A compound as claimed in claim 9, wherein the compound is ethyl (E)-2-(4-hydroxy-3,5-dimethoxyphenyl)vinyl-phosphonofluoridoate of formula:

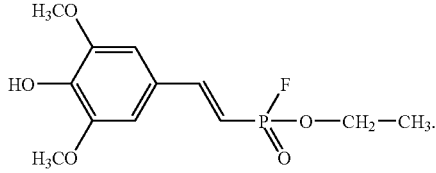

(7)

13. A compound as claimed in claim 9, wherein the compound is ethyl (E)-2-(3,4-dimethoxyphenyl)vinyl-phosphonofluoridoate of formula:

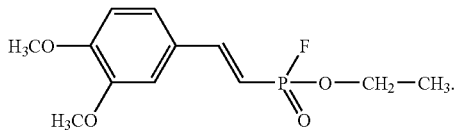

(8)

14. The process as claimed in claim 2, wherein there is used as the fluorinating agent a complex having a molar ratio tertiary amine/hydrogen fluoride of 1:1, denoted $R_3N.HF$.

* * * * *

UNITED STATES PATENT AND TRADEMARK OFFICE
CERTIFICATE OF CORRECTION

PATENT NO. : 7,517,869 B2
APPLICATION NO. : 11/664522
DATED : April 14, 2009
INVENTOR(S) : Michel Baltas et al.

Page 1 of 1

It is certified that error appears in the above-identified patent and that said Letters Patent is hereby corrected as shown below:

Title Page; should read;
--(73) Assignees: Centre National de la Recherche Scientifique (C.N.R.S.), Paris (FR)

Universite Paul Sabatier Toulouse III, Toulouse (FR)--.

Signed and Sealed this

Seventh Day of July, 2009

JOHN DOLL
*Acting Director of the United States Patent and Trademark Office*